United States Patent
Gervasi et al.

(10) Patent No.: US 7,109,365 B2
(45) Date of Patent: Sep. 19, 2006

(54) PROCESSES FOR SOLUBILIZING ORGANOMETALLIC COMPOUNDS IN FLUORINATED SOLVENTS BY ADDITION OF A PARTLY FLUORINATED NON-CATALYTIC CO-SOLUBILIZER

(75) Inventors: David J. Gervasi, West Henrietta, NY (US); Santokh S. Badesha, Pittsford, NY (US); John W. Spiewak, Webster, NY (US)

(73) Assignee: Xerox Corporation, Stamford, CT (US)

( * ) Notice: Subject to any disclaimer, the term of this patent is extended or adjusted under 35 U.S.C. 154(b) by 513 days.

(21) Appl. No.: 10/722,195

(22) Filed: Nov. 25, 2003

(65) Prior Publication Data

US 2005/0113244 A1 May 26, 2005

(51) Int. Cl.
*C07F 49/92* (2006.01)
*C08K 5/15* (2006.01)

(52) U.S. Cl. .................... 556/40; 524/545; 524/546
(58) Field of Classification Search ................ 556/40; 524/545, 546
See application file for complete search history.

(56) References Cited

U.S. PATENT DOCUMENTS

| 6,747,089 | B1 * | 6/2004 | Gervasi et al. | ............. | 524/546 |
| 7,006,780 | B1 * | 2/2006 | Gervasi et al. | ............. | 399/266 |
| 2004/0014853 | A1 * | 1/2004 | Gervasi et al. | ............. | 524/174 |
| 2005/0015936 | A1 * | 1/2005 | Eckert et al. | ............. | 23/295 R |

OTHER PUBLICATIONS

Lehmler et al., Journal of Fluorine Chemistry, vol. 107, No. 1, pp. 141-146 (2001).*
U.S. Appl. No. 10/199,096, filed Jul. 18, 2002, Gervasi et al.
U.S. Appl. No. 10/199,927, filed Jul. 18, 2002, Gervasi et al.
U.S. Appl. No. 10/199,619, filed Jul. 18, 2002, Gervasi et al.

* cited by examiner

*Primary Examiner*—Porfirio Nazario-Gonzalez
(74) *Attorney, Agent, or Firm*—Annette Bade

(57) ABSTRACT

A process for solubilizing an organometallic compound in a fluorinated solvent to form an organometallic solution by adding and reacting a co-solubilizer having a partly fluorinated polymer, an organometallic compound, and a fluorinated solvent, and the co-solubilizer has the ability to cause the organometallic compound to become miscible in a fluorinated solvent, and further, the co-solubilizer is not a catalyst and is present in the final organometallic solution.

20 Claims, No Drawings

PROCESSES FOR SOLUBILIZING ORGANOMETALLIC COMPOUNDS IN FLUORINATED SOLVENTS BY ADDITION OF A PARTLY FLUORINATED NON-CATALYTIC CO-SOLUBILIZER

CROSS-REFERENCE TO RELATED APPLICATIONS

Reference is made to commonly-assigned U.S. patent application Ser. No. 10/721,626, filed Nov. 25, 2003, now U.S. Pat. No. 7,006,780 B2, entitled, "Partially Fluorinated Polymer Coated Development Electrodes," the subject matter of which is hereby incorporated by reference in its entirety.

BACKGROUND

The present invention relates to methods for solubilizing organometallic compounds in fluorinated solvents by addition of a co-solubilizing agent. In embodiments, the co-solubilizing agent is a partly fluorinated co-solubilizer. In embodiments, a fluorinated tail is added to an organometallic compound to cause the organometallic compound to become soluble in a fluorinated solvent. In embodiments, the organometallic compound, which is normally not soluble in fluorinated solvents, becomes completely miscible in fluorinated solvents. Such materials can be used in many arts such as, for example, electrical arts, electrostatographic arts, computer arts, and the like. In embodiments, the organometallic compound and fluorinated solvent solution can be useful as, for example, electrically or thermally conductive soluble fluoropolymer-ceramic hybrids or intermediates, electroluminescent fluorinated fluids or polymer coatings, photosensitive fluorinated fluids or coatings, colored fluorinated fluids or soluble polymer coatings for display devices, fluorinated carrier fluids for metal oxide film formation (where low surface tension of fluorinated fluids are desirable), thermochromic fluorescent or electrochromic fluorinated fluids or coatings, wire coatings such as electrode wire coatings in electrostatographic apparatuses, and many other applications.

In embodiments, the partly fluorinated co-solubilizer does not act as a catalyst, but instead, acts as a filler or additive, and is present in the final solution.

Fluorinated solvents are preferred vehicles for many substances. Fluorinated solvents are preferred because they are thermally insulative, have low surface energy, can have low boiling points, and can be recyclable or recoverable.

A problem results in that many substances are not soluble in fluorinated solvents. For example, many organic molecules and many non-fluorinated or partially fluorinated compounds, are not soluble in fluorinated solvents. Specifically, most, if not all, organometallic compounds, and especially superconductors or superconductor precursors, are not soluble in fluorinated solvents.

Attempts have been made to render previously fluoro-insoluble materials soluble in fluorinated solvents. These attempts include using fluoro-ponytails (e.g., long carbon chains consisting mainly of perfluoroalkyl segments) as co-solvents. These ponytails greatly increase solubility in the fluorous phase. Many approaches are discussed below. However, in all these approaches, the co-solvent is used as a catalyst and can be separated at the end of the reaction.

However, it is sometimes desired that a fluoro-solubilizing co-solvent not be used as a catalyst as it is used in the above listed experiments. This is necessary when it is not suitable to include the step of separating the catalyst from the fluorinated solution. Such a situation may include creating a coating by mixing several compounds together.

SUMMARY

Embodiments of the present invention include: a process for solubilizing an organometallic compound in a fluorinated solvent to form an organometallic solution, comprising adding and reacting a co-solubilizer comprising a partly fluorinated polymer, an organometallic compound, and a fluorinated solvent, wherein the partly fluorinated co-solubilizer has the ability to cause the organometallic compound to become miscible in a fluorinated solvent, and wherein the partly fluorinated co-solubilizer does not react as a catalyst and is present in the organometallic solution.

Embodiments further include: a process for solubilizing an organometallic compound in a fluorinated solvent to form an organometallic solution, comprising adding and reacting a partly fluorinated co-solubilizer, an organometallic compound selected from the group consisting of a superconductor and superconductor precursor, and a fluorinated solvent, wherein the co-solubilizer has the ability to cause the organometallic compound to become miscible in the fluorinated solvent, and wherein the partly fluorinated co-solubilizer is not a catalyst and is present in the organometallic solution, and further wherein the partly fluorinated co-solubilizer has the following formula I:

$R_1-(CF_2)_n-R_2$ wherein n is a number of from about 0 to about 25; $R_1$ and $R_2$ are the same or different and each is selected from the group consisting of $CF_3$, hydrogen, hydroxyl, hydroxyalkyl, aminoalkyl, aminoaryl, aryloxy, alkyl, aryl, carboxylic acid, carboxylic acid containing groups having from about 1 to about 25 carbons, carbonyl, alkyl ketone carbonyl, and $CF_3(CF_2)_o(CH_2)_p$, wherein o represents a number of from about 0 to about 25, and p represents a number of from about 1 to about 25; with the proviso that $R_1$ and $R_2$ are not both fully fluorinated.

In addition, embodiments include: a process for solubilizing an organometallic compound in a fluorinated solvent to form an organometallic solution, comprising adding and reacting a partly fluorinated co-solubilizer, an organometallic compound, and a fluorinated solvent, wherein the partly fluorinated co-solubilizer has the ability to cause the organometallic compound to become miscible in the fluorinated solvent, and wherein the partly fluorinated co-solubilizer does not act as a catalyst and is present in the organometallic solution, and further wherein the partly fluorinated co-solubilizer has the following formula III:

$CF_3(CF_2)_q(CH_2)_r-COOH$ wherein q is a number of from about 0 to about 25, and r is a number of from about 1 to about 25.

DETAILED DESCRIPTION

The present invention relates to methods for solubilizing organometallic compounds in fluorinated solvents by addition of a co-solubilizing agent. In embodiments, the co-solubilizing agent is a partly fluorinated co-solubilizer. In embodiments, a fluorinated tail is added to an organometallic compound to render soluble the organometallic compound in a fluorinated solvent. In embodiments, the organometallic compound, which is normally not soluble in fluorinated solvents, becomes completely miscible in fluorinated solvents due to the addition of the partly fluorinated co-solubilizer. In embodiments, the fluorinated co-solubilizer does not act as a catalyst, but instead, acts as a filler or additive, and is present in the final organometallic composition. In embodiments, a co-solubilizer comprises a partly fluorinated polymer.

The term "partly fluorinated polymers" as used herein, refers to fluorinated polymers that are not completely fluorinated, and contain units or chains other than fluorinated chains. The partly fluorinated polymers may comprise hydrocarbon chains, hydrocarbon units, hydrocarbon substituents, or any carbon-hydrogen bonds, inserted within or adjacent to units containing carbon-fluorine bonds and to units containing other carbon-hydrogen bonds, provided that the resulting partly fluorinated polymer has sufficient chemical and thermal stability to satisfy the process and use requirements. In embodiments, the partly fluorinated polymers are soluble in fluorinated solvents. In embodiments, the partly fluorinated polymers may be amorphous, thereby giving them excellent light transmission properties. In embodiments, the partly fluorinated polymers are solution-coatable and have a low surface energy, and therefore, smooth, thin and uniform low surface energy coatings can result.

A co-solubilizer is a substance, which when added to a mixture renders the solute of that mixture soluble by reaction with the solute. A co-solubilizer is normally soluble in the solvent. Without the co-solubilizer, the solute would otherwise not be soluble in the solvent.

Examples of suitable co-solubilizers comprising a partly fluorinated polymer include a partly fluorinated polymer having the following Formula I:

$$R_1-(CF_2)_n-R_2$$

wherein n represents a number of from about 0 to about 25, or from about 1 to about 10, or from about 1 to about 5; $R_1$ and $R_2$ are the same or different and each is selected from the group consisting of $CF_3$; hydrogen; hydroxyl; hydroxyalkyl having from about 1 to about 25 carbons, or from about 1 to about 10 carbons, or from about 1 to about 5 carbons; aminoalkyl having from about 1 to about 25 carbons, or from about 1 to about 10 carbons, or from about 1 to about 5 carbons; aminoaryl having from about 4 to about 14 carbons or from about 6 to about 10 carbons; aryl having from about 4 to about 14 carbons or from about 6 to about 10 carbons; aryloxy having from about 4 to about 14 carbons, or from about 6 to about 10 carbons; alkyl having from about 1 to about 25 carbons, or from about 1 to about 10 carbons, or from about 1 to about 5 carbons such as methyl, ethyl, propyl, butyl, pentyl and the like; carboxylic acid; carboxylic acid containing groups having from about 1 to about 25 carbons, or from about 1 to about 10 carbons, or from about 1 to about 5 carbons; carbonyls and alkyl carbonyls and alkyl ketone carbonyls each having from about 1 to about 25 carbons, or from about 1 to about 10 carbons, or from about 1 to about 5 carbons; and $CF_3(CF_2)_o(CH_2)_p$, wherein o is a number of from about 0 to about 25, and p is a number of from about 1 to about 25; with the proviso that $R_1$ and $R_2$ are not both fully fluorinated.

In embodiments, $R_1$ and/or $R_2$ is a carboxylic acid or a carboxylic acid containing group having the following formula II:

wherein q is a number of from about 1 to about 25, or from about 1 to about 10, or from about 1 to about 5. In further embodiments, the co-solubilizer has the following formula III:

wherein r is a number of from about 0 to about 25, or from about 1 to about 25, or from about 1 to about 10, and s is a number of from about 1 to about 25, or from about 1 to about 10, or from about 1 to about 5. Examples of partly fluorinated co-solubilizers falling within this formula include partly fluorinated co-solubilizers such as $CF_3(CF_2)_2(CH_2)_2COOH$, and the like, and mixtures thereof.

In embodiments, $R_1$ and/or $R_2$ is a hydroxyalkyl having from about 1 to about 25 carbons, or from about 1 to about 10 carbons, or from about 1 to about 5 carbons. Examples of partly fluorinated co-solubilizers falling within this formula include those selected from the group consisting of $H(CF_2)_6CH_2OH$, $H(CF_2)_{10}CH_2OH$, $HOCH_2(CF_2)_3CH_2OH$, $CHF_2(CF_2)CH_2OH$, $CF_3CHFCF_2CH_2OH$, $CF_3(CF_2)CHOHCH_3$, and mixtures thereof.

In embodiments, in formula I, $R_1$ and/or $R_2$ is selected from the group consisting of alkyl carbonyl having from about 1 to about 25 carbons, or from about 1 to about 10 carbons, or from about 1 to about 5 carbons; carbonyls having from about 1 to about 25 carbons, or from about 1 to about 10 carbons, or from about 1 to about 5 carbons; or alkyl ketone carbonyl having from about 1 to about 25 carbons, or from about 1 to about 10 carbons, or from about 1 to about 5 carbons.

Other examples of suitable partly fluorinated co-solubilizers include 4-aminononafluorobiphenyl, 4-amino-2,3,5,6-tetrafluorobenzoic acid or 1H,1H,11H-eicosafluoroundecyl acrylate and mixtures thereof.

The partly fluorinated coating material is present in the organometallic solution in an amount of from about 0.1 to about 40 percent by weight of total solids, or from about 2 to about 15 percent by weight of total solids. Total solids as used herein, refers to the total amount by weight of partly fluorinated material, fillers, additives, organometallic material such as superconductor or superconductor precursor, and other like solid ingredients contained in the organometallic solution.

An organometallic compound may be used herein in the process. In embodiments, the organometallic compound can be a superconductor or superconductor precursor. The term "superconductors" as used herein refers to metals, alloys and compounds which have the ability to lose both electrical resistance and magnetic permeability at or near absolute zero. In other words, superconductors have infinite electrical conductivity at or near absolute zero. Superconductivity does not normally occur in alkali metals, noble metals, ferro- and antiferromagnetic metals. Usually, elements having 3, 5, or 7 valence electrons per atom can be superconductors.

A superconductor precursor is a material that may be processed to form a superconductor. Organometallic compounds are typically processed via chemical vapor deposition (CVD) to produce films which can be either superconductors or can possess other unique properties such as chemochromic or thermochromic properties. MOCVD refers to metal-organic chemical vapor deposition. Organometallics that can be processed to create superconductor films are referred to as superconductor precursors.

Other examples of suitable superconductors include metal oxide superconductors comprising admixtures of metals from Groups IB, IIA, and IIIB of the Periodic Table.

Illustrative materials of such type include the metal oxide superconductors of the yttrium-barium-copper type ($YBa_2Cu_3O_y$) type, the so-called "123" high temperature superconductors (HTSC) materials, wherein y may be from about 6 to about 7.3, as well as materials where Y may be substituted by Nd, Sm, Eu, Gd, Dy, Ho, Yb, Lu, $Y_{0.5}$—$Sc_{0.5}$, $Y_{0.5}$—$La_{0.5}$, and $Y_{0.5}$—$Lu_{0.5}$, and where Ba may be substituted by Sr—Ca, Ba—Sr, and Ba—Ca. Another illustrative class of superconductor materials includes those of the general formula $(AO)_mM_2Ca_{n-1}Cu_nO_{2n+2}$, wherein the A cation can be thallium, lead, bismuth, or a mixture of these elements, m=1 or 2 (but is only 2 when A is bismuth), n is a number of from about 1 to about 5, M is a cation such as barium or strontium, and the substitution of calcium by strontium frequently is observed, as described in "High Tc Oxide Superconductors", MRS Bulletin, January, 1989, pp. 20–24, and "High Tc Bismuth and Thallium Oxide Superconductors," Sleight, A. W., et al., MRS Bulletin, January, 1989, pp. 45–48. Other examples include $YbBa_2Cu_3O_{7-x}$ (see P. P. Edwards et al. *Chemistry Britain,* 1987, pp. 23–26; $Pb_2Sr_2LnCu_3)O_{8-x}$ (see M. O'Keefe et al., *J. Am. Chem. Soc.* 1988, 110, 1506; $La_{2-x}Sr_xCuO_4$ (see Bednorz and Muller, *Z. Phys. B. Cond. Matter,* 1986, 64, pp 189–195, and the like.

Specific examples of superconductors or superconductor precursors include organometallic compounds such as copper (II) hexafluoropentanedionate, copper (II) methacryloxyethylacetonacetonate, antimony ethoxide, indium hexafluoropentanedionate, and the like, and mixtures thereof.

Other organometallic fillers include monodentate, bidentate, or multidentate ligands such as beta-diketonates, cyclopentadienyls, alkyls, perfluoroalkyls, alkoxides, perfluoroalkoxides, and Schiff bases. Other examples of bidentate or multidentate ligands may comprise oxyhydrocarbyl ligands, nitrogenous oxyhydrocarbyl ligands, or fluorooxyhydrocarbyl ligands. The multidentate ligand may be selected from the group consisting of amines and polyamines, bipyridines, ligands of the Formula IV:

wherein G is —O—, —S—, or —NR—, wherein R is H or hydrocarbyl; crown ethers or cryptates; and ligands of the formula $R^0O(C(R^1)_2C(R^2)_2O)_nR^0$, wherein $R^0$ is selected from the group consisting of hydrogen, methyl, ethyl, n-propyl, cyanato, perfluoroethyl, perfluoro-n-propyl, or vinyl; $R^1$ is hydrogen, fluorine, or a sterically acceptable hydrocarbyl substituent; $R^2$ is hydrogen, fluorine or a sterically acceptable hydrocarbyl substituent; n is 4, 5, or 6, and $R^0$, $R^1$ and $R^2$ may be the same or different from each other.

Examples of organometallic additives also include those having the following Formula VII:

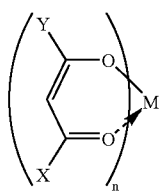

where M may be selected from the group consisting of Al, Ba, Be, Bi, Cd, Ca, Ce, Cr, Co, Cu, Ga, Hf, In, Ir, Fe, Pb, Li, Mg, Mn, Mo, Ni, Pd, Pt, K, Dy, Er, Eu, Gd, Ho, La, Nd, Pr, Sm, Sc, Tb, Tm, Yb, Y, Rh, Ru, Si, Ag, Na, Sr, Ta, Tl, Sn, Ti, V, Zn, Zr, and the like; X or Y may be a hydrocarbon chain having from about 1 to about 30 carbons, or from about 3 to about 12 carbons; a fluorocarbon having from about 1 to about 30 carbons or from about 3 to about 12 carbons, or having from about 1 to about 20 fluorocarbon units of from about 3 to about 8 fluorocarbon units; a substituted or unsubstituted alkoxy group such as methoxy, propoxy, ethoxy, butoxy, pentoxy, and the like; substituted or unsubstituted a cyclic group having from about 4 to about 12 carbons such as cyclobutane, cyclopentane, benzene, a phenyl group such as phenol, cycloheptane, and the like; and wherein n is a number of from about 1 to about 100, or from about 1 to about 20, or from about 1 to about 4.

The organometallic compound can be present in the organometallic solution in any desired amount. Examples of amounts include from about 10 to about 250 parts per hundred, or from about 25 to about 200 parts per hundred, or from about 50 to about 200 parts per hundred organometallic material: polymer.

Any suitable fluorinated solvent may be used. A fluorinated solvent is a solvent comprising fluorine. In embodiments, the fluorinated solvent has low surface energy and low surface tension. Examples of fluorinated solvents include any partially or fully fluorinated organic molecule having a carbon chain with from about 2 to about 25 carbons, or from about 5 to about 15 carbons. The fluorinated solvent may contain carboxylic acid functionality. A specific commercially available example of a suitable fluorinated solvent includes Fluorinert FC-75 from 3M. The fluorinated solvent is added to the organometallic compound and the fluorinated polymer in an amount of from about 1 to about 20 percent, or from about 5 to about 15 percent solution by weight. The fluorinated solvent does not render the organometallic compound soluble.

The process for solubilizing an organometallic compound in a fluorinated solvent to form an organometallic solution includes adding and reacting a partly fluorinated co-solubilizer, an organometallic compound, and a fluorinated solvent. Unlike in known processes, the co-solubilizer does not act like a catalyst. Instead, the co-solubilizer acts as a filler or additive, and is present in the final organometallic solution. In known processes, fluorinated co-solubilizers act as catalysts and are not "used up" in the reaction, and do not become part of the final solution. Instead, in known processes, the fluorinated co-solubilizers can be easily and readily separated out of the final solution. In the present process, the partly fluorinated co-solubilizer is "used up" in the process, is present in the final solution, and is not readily or easily separated out of the final solution. The partly fluorinated co-solubilizer in the present process has the ability to cause the organometallic compound or superconductor or superconductor precursor to become miscible in the fluorinated solvent.

In known processes of fluorous biphase catalysis, the organometallic compound is solubilized in the fluorinated solvent. The catalysis reaction occurs when an aqueous phase (containing reactants) is combined into one single phase at a temperature at which the aqueous phase and a given fluorinated solvent phase are miscible. When the reaction is completed, the temperature of the reaction vessel is then returned to a temperature where the aqueous and fluorinated phase are once again immiscible. The catalyst remains in the fluorinated phase where it can be reused, while the product of the reaction is emulsified or soluble in the aqueous phase.

All the patents and applications referred to herein are hereby specifically and totally incorporated herein by reference in their entirety in the instant specification.

The following Examples further define and describe the embodiments of the invention. Unless otherwise indicated, all parts and percentages are by weight.

EXAMPLES

Example 1

Preparation of Multidentate Ligand in Fluorinated Solvent Solution

An amount of 0.05 grams (0.0001 moles) of an organometallic bidentate ligand (copper II hexafluoropentanedionate) was added to 5.0 grams of 3M Fluorinert FC-75 (a fluorinated solvent). At this point, the superconductor precursor (CuHFP) was not soluble in the fluorinated solvent.

Example 2

Solubilization of Multidentate Ligand in Fluorinated Solvent Solution

To the mixture formed in Example 2, an amount of 0.5 g (approximately 0.0009 moles) of 11H-eicosfluoroundecanoic acid (partially fluorinated co-solubilizer) was added. The resulting combination formed a green-blue solution.

The CuHFP was insoluble in FC-75 (fluorinated solvent) until the 11H-eicosfluoroundecanoic acid (partially fluorinated co-solubilizer) was added.

Example 3

Solubilization of Multidentate Ligand in Fluorinated Solvent Solution

To the solution formed in Example 2, an amount of 5 grams of a 1 weight percent solution of a fully fluorinated polymer (TEFLON® AF 2400) in a fluorinated solvent (FC-75) was added. The resulting solution was blue-green and exhibited no signs of insolubility or immiscibility.

While the invention has been described in detail with reference to specific and preferred embodiments, it will be appreciated that various modifications and variations will be apparent to the artisan. All such modifications and embodiments as may readily occur to one skilled in the art are intended to be within the scope of the appended claims.

What is claimed is:

1. A process for solubilizing an organometallic compound in a fluorinated solvent to form an organometallic solution, comprising adding and reacting a co-solubilizer comprising a partly fluorinated polymer, an organometallic compound, and a fluorinated solvent, wherein said partly fluorinated co-solubilizer has the ability to cause said organometallic compound to become miscible in a fluorinated solvent, and wherein said partly fluorinated co-solubilizer does not react as a catalyst and is present in the organometallic solution.

2. A process for solubilizing an organometallic compound in a fluorinated solvent to form an organometallic solution in accordance with claim 1, wherein the partly fluorinated co-solubilizer has the following formula I:

$R_1$—$(CF_2)_n$—$R_2$ wherein n represents a number of from about 0 to about 25; $R_1$ and $R_2$ are the same or different and each is selected from the group consisting of hydrogen, hydroxyl, hydroxyalkyl, aminoalkyl, aminoaryl, aryloxy, alkyl, aryl, carboxylic acid, carboxylic acid containing groups having from about 1 to about 25 carbons, carbonyl, alkyl ketone carbonyl, and $CF_3(CF_2)_o(CH_2)_p$, wherein o is a number of from about 0 to about 25, and p is a number of from about 1 to about 25, with the proviso that $R_1$ and $R_2$ are not both fully fluorinated.

3. A process in accordance with claim 2, wherein n is from about 1 to about 10.

4. A process in accordance with claim 2, wherein in formula I, $R_2$ is a hydroxyalkyl having from about 1 to about 25 carbons.

5. A process in accordance with claim 4, wherein said partly fluorinated co-solubilizer is selected from the group consisting of $H(CF_2)_6CH_2OH$, $H(CF_2)_{10}CH_2OH$, $HOCH_2(CF_2)_3CH_2OH$, $CHF_2(CF_2)CH_2OH$, $CF_3CHFCF_2CH_2OH$, $CF_3(CF_2)_2CHOHCH_3$, and mixtures thereof.

6. A process in accordance with claim 2, wherein in formula I, $R_2$ is selected from the group consisting of an alkyl carbonyl having from about 1 to about 25 carbons, and an alkyl ketone carbonyl having from about 1 to about 25 carbons.

7. A process in accordance with claim 2, wherein in formula I, $R_2$ is a carboxylic acid.

8. A process in accordance with claim 7, wherein in formula I, $R_2$ has the following formula II:

$(CH_2)_q$—COOH wherein q is a number of from about 1 to about 25.

9. A process in accordance with claim 8, wherein said co-solubilizer is $CF_3(CF_2)_2(CH_2)_2COOH$.

10. A process in accordance with claim 2, wherein said co-solubilizer is selected from the group consisting of 4-aminononafluorobiphenyl, 4-amino-2,3,5,6-tetrafluorobenzoic acid or 1H, 1H, 11H-eicosafluoroundecyl acrylate and mixtures thereof.

11. A process in accordance with claim 1, wherein said partly fluorinated co-solubilizer is added in an amount of from about 0.1 to about 40 percent by weight of total solids.

12. A process in accordance with claim 1, wherein said organometallic compound is selected from the group consisting of monodentate, bidentate, and multidentate ligands.

13. A process in accordance with claim 1, wherein said organometallic compound is selected from the group consisting of a superconductor and a superconductor precursor.

14. A process in accordance with claim 13, wherein said organometallic compound is selected from the group consisting of copper (II) hexafluoropentanedionate, copper (II) methacryloxyethylacetonacetonate, antimony ethoxide, indium hexafluoropentanedionate, and mixtures thereof.

15. A process in accordance with claim 14, wherein said organometallic compound is copper II hexafluoropentanedionate.

16. A process in accordance with claim 1, wherein said fluorinated solvent is a partially fluorinated organic molecule.

17. A process in accordance with claim 1, wherein said fluorinated solvent has from about 2 to about 25 carbons.

18. A process in accordance with claim 1, wherein said fluorinated solvent contains carboxylic acid functionality.

19. A process for solubilizing an organometallic compound in a fluorinated solvent to form an organometallic solution, comprising adding and reacting a partly fluorinated co-solubilizer, an organometallic compound selected from the group consisting of a superconductor and superconductor precursor, and a fluorinated solvent, wherein the co-solubilizer has the ability to cause the organometallic compound to become miscible in the fluorinated solvent, and wherein the partly fluorinated co-solubilizer is not a catalyst and is present in the organometallic solution, and further wherein the partly fluorinated co-solubilizer has the following formula I:

$$R_1\text{—}(CF_2)_n\text{—}R_2$$

wherein n is a number of from about 0 to about 25; $R_1$ and $R_2$ are the same or different and each is selected from the group consisting of hydrogen, hydroxyl, hydroxyalkyl, aminoalkyl, aminoaryl, aryloxy, alkyl, aryl, carboxylic acid, carboxylic acid containing groups having from about 1 to about 25 carbons, carbonyl, alkyl ketone carbonyl, and $CF_3(CF_2)_o(CH_2)_p$, wherein o is a number of from about 0 to about 25, and p is a number of from about 1 to about 25; with the proviso that $R_1$ and $R_2$ are not both fully fluorinated.

20. A process for solubilizing an organometallic compound in a fluorinated solvent to form an organometallic solution, comprising adding and reacting a partly fluorinated co-solubilizer, an organometallic compound, and a fluorinated solvent, wherein the partly fluorinated co-solubilizer has the ability to cause the organometallic compound to become miscible in the fluorinated solvent, and wherein the partly fluorinated co-solubilizer does not act as a catalyst and is present in the organometallic solution, and further wherein the partly fluorinated co-solubilizer has the following formula III:

$$CF_3(CF_2)_q(CH_2)_r\text{—}COOH$$

wherein q is a number of from about 0 to about 25, and r is a number of from about 1 to about 25.

* * * * *